United States Patent [19]

Ghodsian

[11] Patent Number: 4,664,114
[45] Date of Patent: May 12, 1987

[54] DILATOR FOR CERVICAL CANAL

[76] Inventor: Kamran Ghodsian, 69 Woodward St., Roslyn Heights, N.Y. 11577

[21] Appl. No.: 764,788

[22] Filed: Aug. 12, 1985

[51] Int. Cl.$^4$ ............................................. A61M 29/02
[52] U.S. Cl. .................................... 128/344; 604/101; 604/104
[58] Field of Search ............... 128/341, 344, 343, 345; 604/96, 101, 102, 104

[56] References Cited

U.S. PATENT DOCUMENTS

| | | | |
|---|---|---|---|
| 2,687,131 | 8/1954 | Raiche | 604/101 |
| 3,509,884 | 5/1970 | Bell | 604/101 |
| 3,848,602 | 11/1974 | Gutnick | 128/344 |
| 4,089,337 | 5/1978 | Kronner | 604/96 |
| 4,295,464 | 10/1981 | Shihata | 128/344 |
| 4,340,046 | 7/1982 | Cox | 604/96 |
| 4,555,242 | 11/1985 | Saudagar | 604/96 |
| 4,573,966 | 3/1986 | Weikl et al. | 604/101 X |
| 4,596,554 | 6/1986 | Dastgeer | 604/101 X |

Primary Examiner—Robert P. Swiatek
Assistant Examiner—David L. Tarnoff

[57] ABSTRACT

This invention relates to a novel design of a device utilized as a dilator regarding various body cavities, and in particular, the human cervix wherein the device comprises a hollow cylindrical member capable of being inserted through the human cervix and into the uterine cavity such that the inflatable membrane positioned about the exterior of that portion of the device inserted into the uterine cavity is capable of being selectively inflated while the device is in the uterine cavity so as to prevent the inadvertent withdrawal of the device. Additionally, once the device is inserted through the cervix and the inflatable membrane about the exterior portion of the device that is positioned within the uterine cavity has in fact been inflated, there is then caused to be inflated a second inflatable membrane positioned about the exterior of the device that is adjacent to the wall of the cervix so as to cause the selective dilation of the cervix in response to the selective inflating of the second inflatable membrane.

5 Claims, 4 Drawing Figures

DILATOR FOR CERVICAL CANAL

BACKGROUND AND OBJECTS OF THE INVENTION

With regard to present medical practice, there occur a variety of reasons necessitating the dilating of the human female cervix. As a result, there exists in the prior art a variety of means to accomplish same, said means, however, having a variety of drawbacks, both medically, and physically, said prior art devices not addressing themselves to the various advantages inherent in the present invention.

More particularly, it has been the common practice in the prior art in seeking to dilate the human cervix to insert through the cervix opening through a series of insertions, devices of increasing degrees of diameter as one means to achieve said dilation. Additionally, the prior art has also taught the utilization of an absorbent material that is initially inserted into the cervic and upon same absorbing body liquid, or otherwise, it expands, thus dilating the cervix. Furthermore, the prior art has also taught as another means to achieve dilation of the cervix the utilization of inflatable devices, same, however, having various drawbacks as to their operation, all of which are ovrecome by the present invention.

In conjunction with the above, and upon review of the prior art to date, the following patents are representative of the prior art techniques referred to above, to wit, a patent issued to Robert Irvin Leininger, et al, U.S. Pat. No. 3,900,033, entitled DILATOR FOR CERVICAL CANAL; a patent issued to Richard F. Kronser, U.S. Pat. No. 4,089,337, entitled UTERINE CATHETER AND MANIPULATOR WITH INFLATABLE SEAL; and a patent issued to Stanley B. Levy, U.S. Pat. No. 4,490,421, entitled BALLOON AND MANUFACTURE THEREOF.

Although prior art devices and techniques existed, the present invention relates to a novel design of a device utilized as a dilator regarding various body cavities, and in particular, the human cervix, said novel design achieving certain advantages over said prior art devices which are neither taught nor disclosed by said prior art.

It is therefore an object of the present invention to create a novel design for a device utilized as a dilator regarding various body cavities that overcomes the various problems and disadvantages inherent in the prior art devices to date.

It is another object of the present invention to create a novel design for a device utilized as a dilator regarding various body cavities wherein a means is provided to achieve the selective dilating of the human cervix without causing pain nor discomfort to a patient.

It is another object of the present invention to create a novel design for a device utilized as a dilator regarding various body cavities wherein there is achieved the ability to selectively dilated the human cervix by utilization of a device that is not subject to being dislodged inadvertently from the cervix of a patient while the dilating procedure utilizing said device is being accomplished.

It is another object of the present invention to create a novel design for a device utilized as a dilator regarding various body cavities wherein there is achieved the ability by utilization of the device separation of the walls of the uterine cavity without the necessity of utilizing injected liquids and/or gases to achieve same thereby avoiding the adverse effects associated therewith.

It is another object of the present invention to create a novel design for a device utilized as a dilator regarding various body cavities wherein there is the ability to have medical implements inserted through the device for application within the uterine cavity.

It is another object of the present invention to create a novel design for a device utilized as a dilator regarding various body cavities wherein utilization of said device decreases pain and morbidity to the cervix and surrounding body tissue when said device is utilized in accordance with the invention.

It is another object of the present invention to create a novel design for a device utilized as a dilator regarding various body cavities wherein there is achieved the ability to provide a means to inject into the uterine cavity a foreign substance, be it a liquid or a solid, in accordance with prescribed medical treatment.

It is another object of the present invention to create a novel design for a device utilized as a dilator regarding various body cavities wherein said design seeks to achieve an efficient device whose structural integrity is such as to provide an item capable of utilization within the medical field that is easily sterilized, compact in design and whose operation is simple and fool proof.

The objects and advantages of the invention are set forth in part herein and in part will be obvious herefrom, or may be learned by practice of the invention, the same being realized and attained by means of the intrumentalities and combinations pointed out in the appended claims.

The invention consists in the novel parts, constructions, arrangements, combinations and improvements herein shown and described.

SUMMARY OF THE INVENTION

This invention relates to a new and improved design of a device utilized as a dilator regarding various body cavities, and in particular, the human cervix wherein said device comprises a hollow cylindrical member capable of being inserted through the human cervix and into the uterine cavity such that the inflatable membrane positioned about the exterior of that portion of said device inserted into said uterine cavity is capable of being selectively inflated while said device is in said uterine cavity so as to prevent the inadvertent withdrawal of said device. Additionally, once said device is inserted through the cervix and the inflatable membrane about the exterior portion of said device that is positioned within the uterine cavity has in fact been inflated, there is then caused to be inflated a second inflatable membrane positioned about the exterior of said device that is adjacent to the wall of said cervix such that there is provided a means to cause the selective dilation of said cervix in response to the selective inflating of said second inflatable membrane.

The accompaying drawings referred to herein and constituting a part hereof are illustrative of the invention but not restrictive thereof, and, together with the description, serve to explain the principles of the invention.

DESCRIPTION OF A PREFERRED EMBODIMENT

Figure 1:
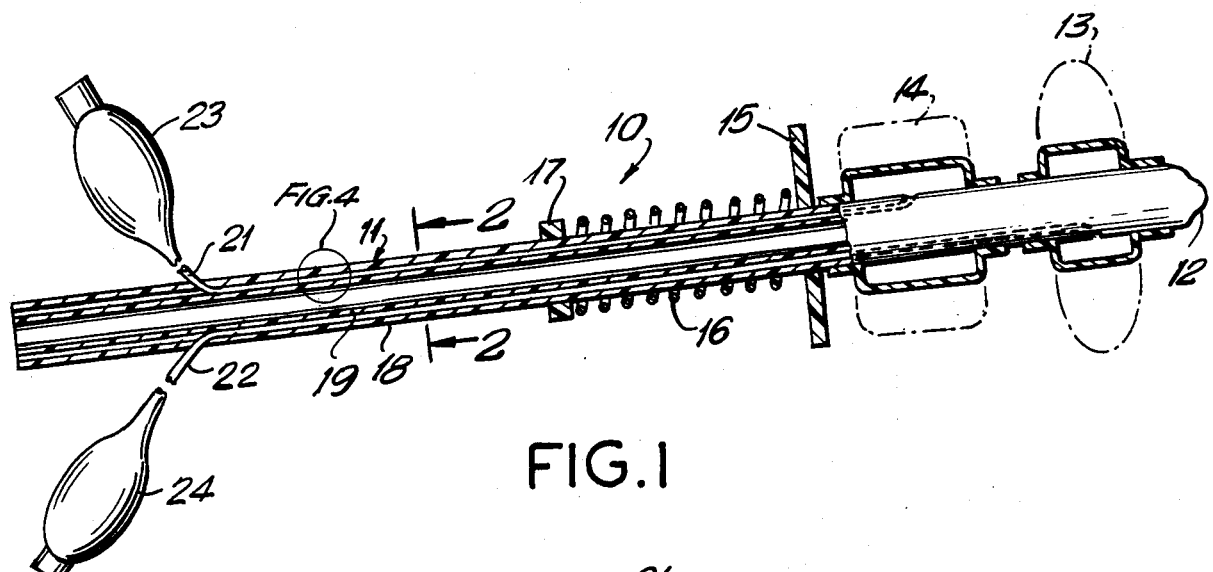
FIG. 1 is a side elevational view in partial cross section of the novel design of a device utilized as a dilator regarding various body cavities, and in particular, the human cervix constructed in accordance with the invention.

Referring now more particularly to the embodiment of the above invention illustrated in the accompanying drawings, there is illustrated in FIG. 1 a front elevational view with a portion thereof being in cross section such that there is generally depicted dilator 10 which is comprised of a double wall cylindrical shaft member 11 that is open at both of its ends, frontal end 12 of said double wall cylindrical shaft member 11 being formed in a fashion as depicted in FIG. 1 so as to provide for a sloped conical cross section such that upon insertion into the human cervix of frontal end 12 of dilator 10 there is avoided the potential of injury to the body tissue as a result of such contact and inward movement.

Affixed about the exterior of double wall cylindrical shaft member 11 near the frontal end 12 of dilator 10 is positioned first inflatable membrane member 13, said membrane capable of being selectively expanded into a donut shaped configuration.

Additionally, a second inflatable membrane member 14 is structurally positioned about the exterior of double wall cylindrical shaft member 11 of dilator 10 of a distance from the location of said first inflatable membrane member 13 such that upon the insertion into the human cervix of dilator 10 and said first inflatable membrane member 13 is positioned within the uterine cavity of a patient, said second inflatable membrane member 14 is physically positioned adjacent to the wall of patient's cervix.

Additionally, disc member 15 is physically affixed about the exterior of double wall cylindrical shaft member 11 at a point back from the location of said second inflatable membrane member 14 and is capable of axial movement parallel to the axis of double wall cylindrical shaft member 11. Immediately adjacent to disc member 15 is coil spring 16, coil spring 16 being structurally affixed about the exterior of double wall cylindrical shaft 11 between disc member 15 and bar member 17, coil spring 16 thus being mechanically confined about the exterior double wall cylindrical shaft 11 but physically positioned between bar member 17 and disc member 15 such that coil spring 16 acts as a dampening means for pressure applied axially to disc member 15 in the direction away from frontal end 12 of dilator 10.

Figure 2:
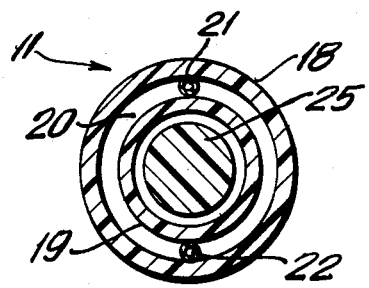
FIG. 2 is a cross sectional view of the dilator depicted in FIG. 1 and taken along lines 2—2.
Figure 4:
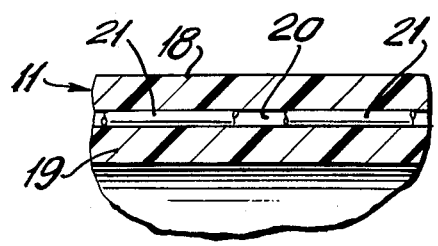
FIG. 4 is a partial cross sectional view of an isolated portion of the dilator depicted in FIG. 1.

Furthermore, and as depicted in FIGS. 2 and 4, outer wall member 18 of double wall cylindrical shaft member 11 and inner wall member 19 of double wall cylindrical shaft member 11 are spaced so as to define cavity 20 there between thereby providing a space through which can travel hollow conduit 21 and hollow conduit 22, one end of hollow conduit 22 being coupled hydraulically to the interior of the cavity defined by said first inflatable membrane member 13 and with the other end of said hollow conduit 22 opening into receptacle chamber 24, receptacle chamber 24, hollow conduit 22 and first inflatable membrane member 13 defining and intact hydraulic system unto itself. Similarly, hollow conduit 21 has one of its ends coupled hydraulically to the interior of the cavity defined by said second inflatable membrane member 14 and with the other end of said hollow conduit 21 opening into receptacle chamber 23, receptacle chamber 23, hollow conduit 21 and second inflatable membrane member 14 defining an intact hydraulic system unto itself.

Figure 3:
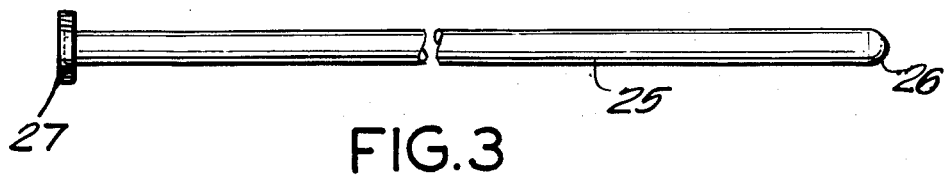
FIG. 3 is a side elevational view of the stylet utilized in conjunction with the dilator depicted in FIG. 1.

Additionally, and as depicted in FIG. 3, stylet 25 is a solid cylindrical member whose diameter is such as to permit stylet 25 to be inserted through the entire length of double wall cylindrical shaft member 11 and to have the front end 26 of stylet 25 protrude beyond frontal end 12 of double wall cylindrical shaft member 11. The front end 26 of stylet 25 is formed to define a blunt surface which assists in avoiding pain, tissue damage and/or discomfort to an individual when dilator 10 is physically inserted into the cervix of a patient.

Cap member 27 is structurally affixed to the end of stylet 25 as depicted in FIG. 3 such that upon the insertion into double wall cylindrical shaft member 11 of stylet 25 such that front end 26 of stylet 25 protrudes out the frontal end 12 of dilator 10, cap member 27 provides an air tight seal about double wall cylindrical shaft member 11.

In actual operation, and in accordance with the present invention, dilator 10 has inserted through double wall cylindrical shaft member 11, stylet 25 such that front end 26 of stylet 25 protrudes out frontal end 12 of double wall cylindrical shaft member 11 and cap member 27 provides an air tight seal about the heretofore opened end of double wall cylindrical shaft member 11. Neither said first inflatable membrane member 13 nor second inflatable membrane member 14 are inflated at this time. As so assembled, dilator 10 is now ready for insertion into the cervix of a patient. Upon insertion of dilator 10 into the cervix of a patient, dilator 10 is inserted up to the point where disc member 15 prevents the further insertion into said cervix of dilator 10.

Due to the preconceived design of the invention, disc member 15, said first inflatable membrane member 13 and second inflatable membrane member 14 are thus physically positioned within the female body such that said first inflatable membrane member 13 is within the uterine cavity of the patient and said second inflatable membrane member 14 is adjacent to the wall of the patient's cervix.

By the insertion of a fluid or air into receptacle chamber 24 by way of a hypodermic needle, or otherwise, first inflatable membrane member 13 is inflated within the uterine cavity of the patient, and as such, provides an obstacle to having dilator 10 physically withdrawn from the patient's uterine cavity. As such, there is now provided the stable placement of dilator 10 in conjunction with the patient's body as well as a mechanical means to separate the walls of the uterine cavity without having liquids or gasses escape into the patient's body and cause discomfort.

Once so positioned, second inflatable membrane member 14 is now caused to be selectively inflated by the injection of a liquid or air into the receptacle chamber 23 by way of a hypodermic needle, or otherwise, and as a result second inflatable membrane member 14 is caused to inflate and thus physically press against the walls of the patient's cervix, thereby achieving the opening of said cervix to any deired diameter.

In keeping with the invention, once having caused the opening of the cervix, dilator 10 can be withdrawn by deflating said first inflatable membrane member 13 and said second inflatable membrane 14, same achieved by the withdrawing of the liquid or air heretofore injected into receptacle chambers 24 and 22 respectively by way of a hypodermic needle, or otherwise, and then withdrawing dilator 10 from the patient's cervix. By so doing, the cervix remains open to the expanded diameter and the walls of the uterine cavity remain separated and the patient is thus ready for any medical procedure requiring access to the uterine cavity through the cervix.

As an alternative means of treatment of a patient utilizing dilator 10, upon having dilator 10 so positioned with said first inflatable membrane member 13 and said second inflatable membrane member 14 so inflated, stylet 25 can be removed from within double wall cylindrical shaft member 11 thereby providing a conduit into the uterine cavity through the hollow opening defined by double wall cylindrical shaft member 11. In this manner various medical implements can be inserted safely into the human cervix so as to carry out various medical procedures in a manner that overcomes many of the inconveniences and drawbacks associated with prior art devices.

In keeping with the invention, it is also within the scope thereof to utilize cap member 27 separate and apart from stylet 25 so as to provide an air tight seal about the externally exposed end of double wall cylindrical shaft member 11 once dilator 10 has been procedurally placed through the cervix of a patient and within said patient's uterine cavity. Furthermore, cap member 27 can contain an opening through its center that is compatible with having inserted there through once said cap is affixed in an air tight fashion about double wall cylindrical shaft member 11 medical instruments utilized for various medical procedures that are to occur within the uterine cavity, the opening formed in cap member 27 being such so as to provide an air tight seal about the medical instrument being utilized.

The preceding description and accompanying drawings relate primarily to a specific embodiment of the invention, and the invention in its broader aspect should not be so limited to one specific embodiment as herein shown and described, but departures may be made therefrom within the scope of the accompanying claims without departing from the principals of the invention and without sacrificing its chief advantages.

I claim:

1. A dilator for utilization in conjunction with various medical procedures associated with the human cervix and uterine cavity, said dilator comprising:
   (a) a first hollow cylindrical shaft member;
   (b) a second hollow cylindrical shaft member axially aligned about said first hollow cylindrical shaft member so as to define a spacing there between, said second hollow cylindrical shaft member and said first hollow cylindrical shaft member being structurally affixed to each other so as to form a stable unitary structure;
   (c) a first inflatable membrane member structurally affixed to the exterior of said second cylindrical shaft member at the end of said second cylindrical shaft member that is inserted into said uterine cavity, said first inflatable membrane member being capable of being selectively inflated to a size capable of separating the walls of said uterine cavity so as to allow for the occurrence of various medical procedures;
   (d) a second inflatable membrane member structurally affixed to the exterior of said second cylindrical shaft member at a location on said second cylindrical shaft member adjacent to the location of said first inflatable membrane member said second inflatable membrane member being capable of selective inflation to a diameter less than the diameter to which said first inflatable membrane member is capable of being inflated to;
   (e) a first means for selectively inflating said first inflatable membrane member, said first means comprising a closed hydraulic system having a first receptacle chamber exterior to said second hollow cylindrical shaft member and a first hollow conduit member hydraulically coupling said first receptacle chamber to said first inflatable membrane member, said first hollow conduit member being positioned within the spacing defined between said first hollow cylindrical shaft member and said second hollow cylindrical shaft member;
   (f) a second means for selectively inflating said second inflatable membrane member, said second means comprising a closed hydraulic system having a second receptacle chamber exterior to said second hollow cylindrical shaft member and a second hollow conduit member hydraulically coupling said second receptacle chamber to said second inflatable membrane member, said second hollow conduit member being positioned within the spacing defined between said first hollow cylindrical shaft member and said second hollow cylindrical shaft member; and
   (g) a stylet comprising a cylindrical shaft member whose front end is blunt in configuration, and a cap member structurally affixed to the end of said cylindrical shaft member at its end opposite to said blunt end, said stylet being capable of being selectively inserted through said first hollow cylindrical shaft member so that said blunt end of said stylet protrudes out of said first hollow cylindrical shaft member adjacent to said first inflatable membrane member prior to inserting said dilator into said human cervix and uterine cavity, said cap member being capable of providing an airtight seal about said second hollow cylindrical shaft member when said stylet has been inserted through said first hollow cylindrical shaft member such that said blunt end of said stylet is protruding out of said first hollow cylindrical shaft member.

2. A dilator for utilization in conjunction with various body cavities as described in claim 1, wherein there is structurally affixed about the exterior of said hollow cylindrical shaft member adjacent to said second inflatable membrane member a disc member capable of movement parallel to the axis of said hollow cylindrical shaft member.

3. A dilator for utilization in conjunction with various body cavities as described in claim 2, wherein means are provided to dampen the movement parallel to the axis of said hollow cylindrical shaft member of said disc member.

4. A dilator for utilization in conjunction with various body cavities as described in claim 1, wherein said first inflatable membrane member upon being inflated takes on the structural shape of a donut.

5. A dilator for utilization in conjunction with various body cavities as described in claim 1, wherein said second inflatable membrane member upon being inflated takes on a shape whose cross section is rectangular in appearance.

* * * * *